(12) United States Patent
Lippman

(10) Patent No.: US 10,953,074 B2
(45) Date of Patent: Mar. 23, 2021

(54) COMPOSITION AND METHOD FOR IMPROVING SENSORINEURAL HEARING

(71) Applicant: Richard D. Lippman, Honolulu, HI (US)

(72) Inventor: Richard D. Lippman, Honolulu, HI (US)

(*) Notice: Subject to any disclaimer, the term of this patent is extended or adjusted under 35 U.S.C. 154(b) by 142 days.

(21) Appl. No.: 15/401,076

(22) Filed: Jan. 8, 2017

(65) Prior Publication Data

US 2018/0193424 A1    Jul. 12, 2018

(51) Int. Cl.
*A61K 38/37*    (2006.01)
*A61K 38/18*    (2006.01)
*A61K 38/27*    (2006.01)

(52) U.S. Cl.
CPC .............. *A61K 38/27* (2013.01); *A61K 38/18* (2013.01)

(58) Field of Classification Search
None
See application file for complete search history.

(56) References Cited

U.S. PATENT DOCUMENTS

| 5,855,920 A * | 1/1999 | Chein | A61K 38/27 424/568 |
| 2006/0013858 A1* | 1/2006 | Trune | A61K 31/57 424/427 |
| 2015/0329614 A1* | 11/2015 | Fornaro | C07K 14/65 514/8.6 |

FOREIGN PATENT DOCUMENTS

| FR | WO 02/101002 | * | 12/2002 | |
| IL | WO 2012/104838 | * | 8/2012 | ............. A61K 38/30 |

OTHER PUBLICATIONS

Baretto et al., Braz J Otorhinolaryngol. 2016; 82: 353-364. (Year: 2016).*
Yamahara et al., Hearing Research, 2015; 330: 2-9 (Year: 2015).*
Attias et al., Eur Arch Otorhinolaryngol, 2012; 269: 461-466. (Year: 2012).*
Nakagawa et al., BMC Medicine, 2010; 8: 76. (Year: 2010).*
Perrini et al., Journal of Endocrinology, 2010; 205: 201-210 (Year: 2010).*

* cited by examiner

*Primary Examiner* — Christina M Borgeest
(74) *Attorney, Agent, or Firm* — Andrew S. Dallmann

(57) ABSTRACT

The present invention is directed to compositions and methods for improving hearing parameters in a human (including hearing volume, hearing range and word recognition) by reversing or inhibiting damage to cochlear cells caused by toxic byproducts of oxygen metabolism. In a preferred embodiment, a pharmaceutically acceptable composition containing insulin-like growth factor one (IGF-1) and human growth hormone (HGH), or their derivatives in a 5:2 ratio by weight, is topically administered every three days in a dosage of 0.1 to 2 mcg per kilogram of body weight. The composition directly penetrates the inner ear and cochlea to provide greater regulation of sodium and potassium levels in the delicate sound-detecting hair cells. In accordance with the present invention, mean word recognition was improved by nearly 39 percent, hearing volume was improved by up to 40 dB, and the hearing range was improved above 6,000 Hz.

9 Claims, 7 Drawing Sheets

COMPOSITION AND METHOD FOR IMPROVING SENSORINEURAL HEARING

FIELD OF THE INVENTION

The present invention relates to compositions and methods for improving hearing parameters associated with sensorineural hearing loss in mammals.

BACKGROUND OF THE INVENTION

Senescence is the condition or process of deterioration with age, including progressive, multi-system organ degradation or "cell drop-out" which is the apoptosis or disappearance of cells and consequent shrinkage of the body's organs. Such organ shrinkage is seen in autopsies on the aged. For example, the human brain can decrease from an average weight of 1,500 grams in a young human adult to 1,000 grams or less in a human of advanced age. A brain that has decreased in size (the senescent brain) is highly forgetful, is unable to memorize new information and cannot react quickly to external stimulae. Shrinkage with age is also found in other human organs such as the cochlea, heart, liver, kidneys, lymph nodes, skeletal muscles and vertebrae. Such shrinkages often correspond to the accumulation of peroxidized, free radical products seen as brown-yellow age pigment (lipofuscin). Other corresponding changes that are associated with aging are hearing loss, wrinkled skin, depleted fat deposits, fewer dermal melanocytes, brittle bones, low infection resistance, poor exercise tolerance and lack of reproductive ability. Sixty-three percent of Americans age 70 and above suffer from sensorineural hearing loss, a disease of aging.

At the cellular level, sensorineural hearing loss means inadequate DNA repair leading to disordered and/or nonexistent cell replication, loss of mitotic control factors in the nucleus and cytoplasm including disordered nuclear cytoplasmic exchange, and permanent closing of microcirculatory capillary beds, especially in human cochlea, resulting in focal cell drop-out and loss of cell and organelle membrane function. This progressive cellular process affects all organs and tissues throughout the body and its etiology and pathogenesis must therefore involve a universal and fundamental aspect of cell physiology. Aging of the human cochlea and the mammalian organism as a whole must be examined at the cellular level because changes of individual cells affect changes in individual body organs and changes in individual body organs affect the organism as a whole. For example, death or dysfunction of a critical bodily organ, such as the heart, will result in the death of the body as a whole.

In any study on aging two distinct types of cells must be considered: normally dividing cells and post-mitotic cells. Normally dividing cells are those of the skin, hair and gastrointestinal tract, for example. While thousands of such cells die daily, they are continually replaced. Their replacement is with nearly exact replicas until the time of aging or senescence begins. This time begins in the mid-twenties in man. The second cell type, i.e. post-mitotic cells, are those that make up the cochlea, heart, brain, and central nervous system, for example. Generally speaking, post-mitotic cells do not divide or reproduce. Mammals are born with a fixed number of post-mitotic cells that lose function and die daily throughout a mammal's life span. Death of a mammal occurs when a critical number of post-mitotic cells lose function or die in a critical organ, e.g. the brain.

Biomedical gerontological research has provided some theories regarding the metabolic course of events, which leads to the inevitable loss of function, deterioration, destruction, apoptosis, and death of mammalian cells. One theory relates to mammalian cellular metabolism's reliance on oxygen metabolism. By "oxygen metabolism" is meant the burning of oxygen in the cells' energy factories (mitochondria) together with foods such as fatty acids to produce adenosine triphosphate (ATP), the cell's energy source. Production of ATP occurs continually through enzymatically controlled chemical reactions. Unfortunately, these chemical reactions are not 100% efficient. For example, in the bacteria, *E. coli*, these reactions are only approximately 84% efficient. As one moves up the scale of evolution, these reactions become increasingly more efficient.

Most hearing loss cases are caused by the aforementioned degradation or functional impairment of the approximate 15,000 hair cells in the human cochlea. Unfortunately, scientists do not believe that human and mammalian hair cells are capable of proliferation after an infant's birth because they are considered postmitotic (see e.g., Ruben R J, 1967, Development of the inner ear of the mouse: a radio-autographic study of terminal mitoses. *Acta Otolaryngol. Suppl.* 220 pp. 221-244). There are two cell types, i.e. the normally dividing cells and post-mitotic cells. Normally dividing cells are able to reproduce and replace damaged cells. On the other hand, post-mitotic cells are sometimes repaired with hormones after bombardment with toxic oxygen byproducts of oxygen metabolism. Such bombardment often reduces their function, damages their DNA and/or kills them outright. This is a steady-state, linear aging process until damage to DNA and cellular defensive enzymes becomes so great that the aging process acquires an endogenous, accelerating character.

The long term, lifetime effects of this endogenous toxic chemical bombardment can also be exemplified in the progressive loss of hearing, and the wrinkling and hardening of the skin and arteries with age. The cochlear interior and skin and arteries consist of supportive material called collagen and elastin. Collagen is the major protein of the white fibers of connective tissue, cartilage and bone. Elastin, or elastic tissue, is the major connective tissue protein of elastic structures such as the large blood vessels, the skin, and the cochlea. Elastin enables these structures to stretch, and then resume their original shape and size. Collagen and elastin contain fibers internally linked together by chemical bonds called "imide bonds". It is theorized that mammalian aging involves the oxidation of these imide bonds to "amide bonds". In the skin, cochlea, and arterial collagen and elastin of mammals, as more and more amide bonds are formed, the collagen and elastin fibers become increasingly less elastic and flexible. In man, it is known that these fibers harden at a rate of approximately 7% per decade after the age of maturity (approximately mid-twenties). This means that the arterial-vascular system in the ear and systemically has a theoretical life span of approximately 140 years before becoming 100% rigid.

Free radical pathology mechanisms seem to be involved at key points in the etiology and pathogenesis of hearing loss, cancer, occlusive atherosclerosis and wrinkling of the skin. Free radical pathology ensues largely from free radical and oxidation products that negatively affect cell membranes, collagen, elastin, immune functions, microcirculation, nucleic acids and regulatory proteins such as insulin-like growth factor one. Scientific studies have shown that this mechanism progresses from inciting factors to free radical pathologic reactions that damage organelles, cells and tissues resulting in aging and disease. Aging seems to affect simultaneously all cells, tissues and organs throughout the body in an insidious, progressive pattern whose pathogenesis and etiology therefore are thought to involve a fundamental and universal aspect of cell physiology.

The clinical significance of toxic free radicals and oxidative agents generated endogenously in living cells has been documented in various scientific and medical publications. An association between these toxic agents and aging has been observed. It is therefore desired that compositions and techniques be provided for reversing hearing loss and inhibiting or reversing aging of the human cochlea and thereby improving various hearing parameters. Such methods desirably include systemic treatment of humans to inhibit aging of the entire body as well as non-invasive treatment, e.g., to inhibit or reverse hearing loss in sensitive cochlear hair cells.

SUMMARY OF THE INVENTION

The present invention is directed to methods and compositions for improving hearing parameters (including hearing volume, hearing range and word recognition) by reversing or inhibiting damage to human cochlear cells caused by toxic byproducts of oxygen metabolism. In a preferred embodiment of the invention, a pharmaceutically acceptable composition containing IGF-1 (or its derivatives) and human growth hormone (or its derivatives), in a 5:2 ratio by weight, is topically administered every three days to a human in a dosage of 0.1 to 2 mcg of IGF-1 per kilogram of body weight. The composition is able to directly penetrate the inner ear and cochlea with IGF-1 and human growth hormone. With this direct transdermal penetration and absorption, hormones provide greater regulation of sodium and potassium levels in the delicate sound-detecting hair cells. The composition was also shown to improve word recognition in patients with IGF-1 and HGH deficiencies. The IGF-1 polypeptide derivatives useful in practice of principles of this invention may be represented by approximately 70 amino acids in a single chain with three intramolecular disulfide bridges and an approximate molecular weight of 7,649 Dalton. The preferred compounds of this polypeptide chain include somatomedin C, mecasermin, and Increlex. The HGH polypeptide derivatives useful in practice of principles of this invention may be represented by approximately 191 amino acids in a single chain with two intramolecular disulfide bridges and an approximate molecular weight of 22,124 Daltons. The preferred compounds of this polypeptide chain include human growth hormone and somatotropin.

DETAILED DESCRIPTION

Figure 1:
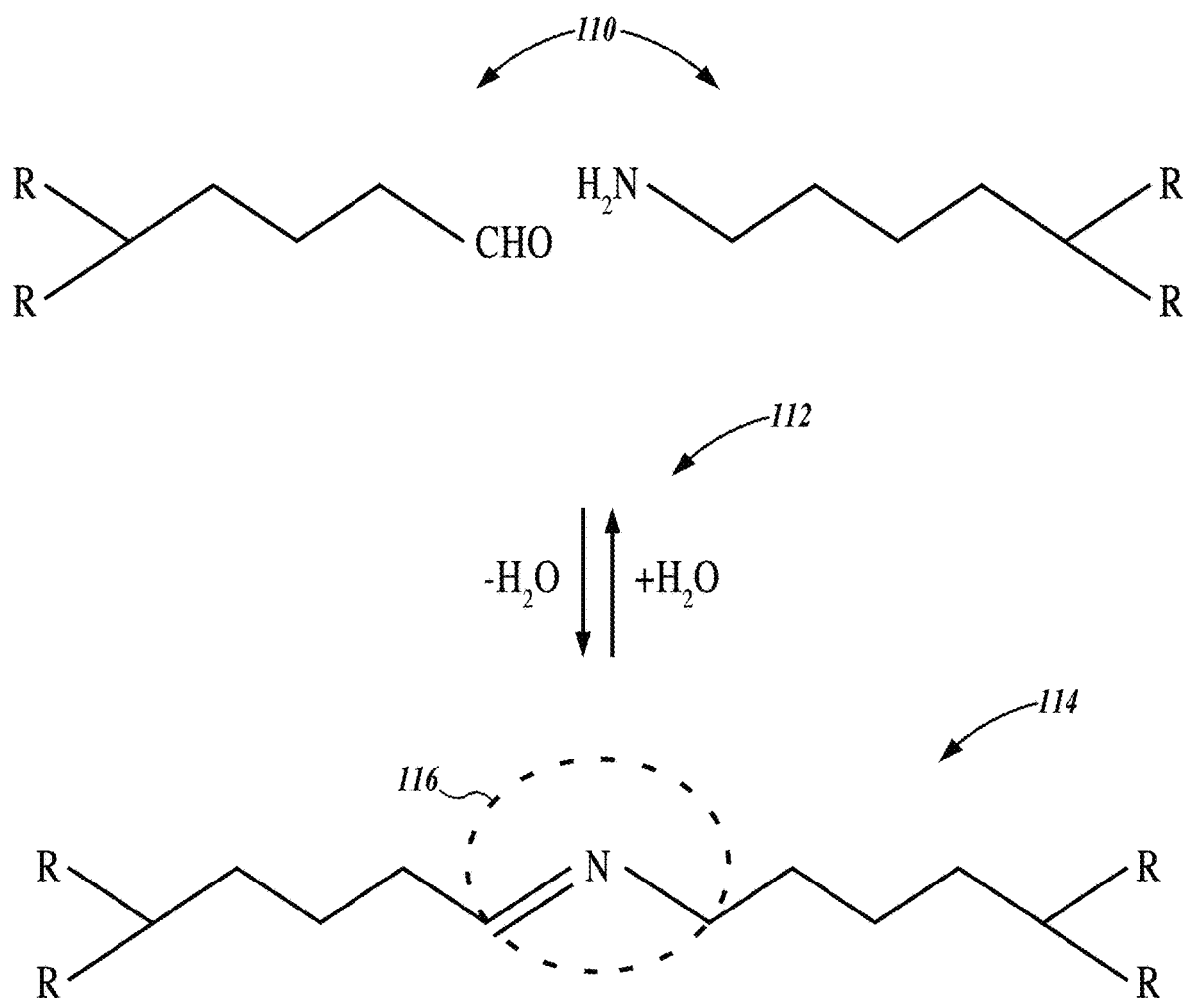
FIG. 1 is a schematic representation of two collagen fibers (R) or of two elastin fibers (R) lying side by side, showing a reversible imide bond linking them together.

In the following discussion, numerous specific details are set forth to provide a thorough understanding of the present invention. However, those skilled in the art will appreciate that the present invention may be practiced without such specific details. In other instances, well-known elements, processes or techniques have been briefly mentioned and not elaborated on in order not to obscure the present invention in unnecessary detail and description. Moreover, specific details and the like may have been omitted inasmuch as such details are not deemed necessary to obtain a complete understanding of the invention, and are considered to be within the understanding of persons having ordinary skill in the relevant art.

The present invention relates to the use of pharmaceutically acceptable compositions that include effective amounts of polypeptide derivatives as the active ingredient for retarding and reversing the degenerative process of sensorineural hearing loss in mammals (particularly humans) and thereby improving hearing parameters such as hearing volume, hearing range and word recognition. More specifically, the present invention discloses pharmaceutically acceptable compositions of IGF-1 and human growth hormone and methods to achieve improved mean word recognition by about 38.85 percent, improved hearing volume by up to 40 dB, and improved hearing range above 6,000 Hz. The hearing range can be defined as the range of frequencies that can be effectively heard. Compositions of IGF-1 and human growth hormone dissolved in a suitable topical carrier (e.g. cream, serum or lotion, see Examples 3 and 4 below) yielded significant improvement in word recognition and hearing volume up to 40 dB. Research in connection with the present invention revealed that, to achieve a preferred clinical effect, IGF-1 and HGH must be allowed to cycle intratympanically between high and low concentrations. This IGF-1 and HGH cycling results in a high concentration absorbed into the cochlea. Subsequently, on intermittent days, the formula is not applied, and this inaction allows cochlear levels to fall to low concentration levels. This intratympanic high and low cycling allows the cochlear receptor sites such as IGF-1-R to recharge or reboot which in turn allows for a more optimal clinical effect, namely improved hearing up to 40 dB and near normal word comprehension of 48 out of 50 monosyllable words. In a preferred embodiment, a treatment frequency (topical application) of once every three days was determined to be preferred for optimal results in accordance with the present invention. The present invention contemplates the use of IGF-1, human growth hormone, and derivatives and metabolites thereof. In an exemplary embodiment, the composition used in accordance with the present invention includes the hormone aldosterone, which is a metabolite of IGF-1 and human growth hormone.

Further, it has been determined that the IGF-1 should be combined with human growth hormone in a 5 to 2 ratio (by weight). Thus, by correcting for IGF-1 deficiencies, hearing improves by more than a resounding 30 dB with improvement in word recognition. The research in connection with the present invention showed temporary improvements in hearing by as much as 40 dB. Conventional hearing aids do not meet these standards. Indeed, hearing aids are limited to improving only hearing volume and not word recognition, and perhaps at the cost of too loud and damaging sound amplification in the ears. Remedies tested by other researchers in the field have yielded only marginal improvement in hearing volume.

The term "aging" as used herein generally means any damage to the cells caused by toxic byproducts of oxygen metabolism. Such aging can, for example, result from partial damage or complete destruction of cells or from the conversion of imide bonds to amide bonds in human collagen and/or elastin resulting in hardening of the arteries or skin wrinkling, the apoptosis of sensitive human cochlear hair cells, etc. Thus, the phrases "inhibiting aging" or "retarding aging" means inhibiting or retarding damage to cochlear hair cells caused by toxic byproducts of oxygen metabolism. Reference to "cochlear hair cells" means the mechanosensory hair cells of the cochlea (the auditory system) and of the saccule, utricle, crista ampularis, and semicircular canals (the vestibular system), which contribute to detecting and amplifying sound and to maintaining balance, respectively. Hair cells resemble columnar cells, each with a hair bundle of stereocilia at the apical surface. The deflection of the stereocilia opens mechanically gated ion channels that allow small, positively charged ions (primarily potassium and calcium) to enter the hair cell. Unlike many other electrically active cells, the hair cell itself does not fire an action potential. Rather, the influx of positive ions such as calcium and potassium depolarizes the cell, resulting in a normal receptor potential of approximately 80 mV. As such, hair cells typically show a graded electrical response rather than action potential spikes typical of other neurons.

The polypeptide used in accordance with the present invention is IGF-1 and its derivatives, which are characterized by having 70 amino acids in a single chain with three intramolecular disulfide bridges and an approximate molecular weight of 7,649 Daltons. For ease of reference, this polypeptide chain will be referred to as "Formula (1)" or "IGF-1 and its derivatives." The preferred compounds of this polypeptide chain include somatomedin C, mecasermin, and Increlex. In an exemplary embodiment, these polypeptides have the following atomic composition: C331, H512, N84, O101, and S7. Three disulfide bridges are essential to the bioactivity of this structure, and loss of any of these three disulfide bridges renders the molecule biologically inert.

Also included is a polypeptide chain of human growth hormone (HGH or hGH) and its derivatives. The preferred compounds of this polypeptide chain include somatotropin. In an exemplary embodiment, these polypeptides have the following atom composition: C39, H60, N8, and O13. Two disulfide bridges are essential to the bioactivity of this structure, and loss of any of these two disulfide bridges renders the molecule biologically inert.

Destruction of these disulfide bridges often occurs by a process of chemical oxidation and/or free radical attack. These disulfide bridges will oxidize and the three-dimensional structure will collapse if the molecule is dissolved in water and stored at ambient (room temperature) for a period of approximately 12 hours. Thus, IGF-1 and HGH dissolved in water should optimally be stored at refrigerator temperatures (+5° C.) and in the dark to prevent oxidation and photo-chemical deterioration and collapse of the three disulfide bridges. The disulfide bond is the weakest of all covalent bonds and is subject to attack and degradation when a disulfide bridge becomes an electron "sink" or free radical electron acceptor and denatured by radicals such as hydroxyl (•OH) radicals and other toxic byproducts of cell oxygen metabolism.

In accordance with the present invention, an important feature of the polypeptide chain Formula (1) and HGH is that they have highly active and desirable zwitterons per molecule. None of the other known peptide substances previously disclosed in the art are useful to retarding/inhibiting hearing loss to achieve at least 40 dB of improved hearing volume. These zwitterons function by increasing lipophilicity of the peptide chain, thus allowing desirable transportation through membranes.

Pharmaceutical Compositions

Suitable preparations, e.g., substantially pure preparations of the proteolysis-enhancing agents, optionally together with one or more additional active agents, may be combined with pharmaceutically acceptable carriers, diluents, solvents, etc., to produce an appropriate pharmaceutical composition. Methods and ingredients for producing pharmaceutical compositions are utilized for the present invention as known in the art. It is to be understood that the pharmaceutical compositions of the invention, when administered to a subject, are typically administered for a time and in an amount sufficient to treat the disease or condition for whose treatment they are administered. Exemplary suitable modes of administration and formulations are described herein.

Further provided are pharmaceutically acceptable compositions comprising a pharmaceutically acceptable derivative (e.g., a prodrug) of any of the agents of the invention, by which is meant any non-toxic salt, ester, salt of an ester or other derivative of an agent of this invention that, upon administration to a recipient, is capable of providing, either directly or indirectly, an agent of this invention or an active metabolite or residue thereof. As used herein, the term "active metabolite or residue thereof" means that a metabolite or residue thereof also possesses similar activity to the parent agent. For example, rather than administering an active polypeptide, a zymogen (i.e., an inactive or less active enzyme pre-cursor that requires a biochemical change, such as a hydrolysis reaction revealing the active site, for it to become an active enzyme) could be administered.

The term "pharmaceutically acceptable carrier, adjuvant, or vehicle" refers to a non-toxic carrier, adjuvant, or vehicle that does not destroy the pharmacological activity of the agent with which it is formulated. Furthermore, it is recognized that preparation methods for the pharmaceutical compositions are typically selected so as to not substantially reduce the activity of the agent with which they are formulated. Pharmaceutically acceptable salts of certain of the agents of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dihydroxy-3,20-dioxopregn-4-en-18-al, dodecyl sulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate, and undecanoate. Other acids, such as oxalic, while not in themselves pharmaceutically acceptable, may be employed in the preparation of salts useful as intermediates. Salts derived from appropriate bases include alkali metal (e.g., sodium and potassium), alkaline earth metal (e.g., magnesium), ammonium and $N+(C1-4$ alkyl$)4$ salts. Also contemplated within the scope of the present invention is the quaternization of any basic nitrogen-containing groups of the compounds disclosed herein. Water or oil-soluble or dispersible products may be obtained by such quaternization.

A pharmaceutical composition is formulated to be compatible with its intended route of administration. Pharmaceutical compositions suitable for injection or infusion typically include sterile aqueous solutions (where water soluble) or dispersions and sterile powders for the extemporaneous preparation of sterile injectable solutions or dispersion. Suitable carriers include physiological saline, bacteriostatic water, water for injection, dextrose solutions, phosphate buffered saline (PBS), or Ringer's solution. Antibacterial and/or antifungal agents; chelating agents, such as ethylenediaminetetraacetic acid; buffers such as acetates, citrates, or phosphates; and agents for the adjustment of tonicity, such as sodium chloride or dextrose, can be included. The pH can be adjusted with acids or bases, such as hydrochloric acid or sodium hydroxide. It may be advantageous to formulate the compositions in dosage unit form for ease of administration and uniformity of dosage. Dosage unit form as used herein refers to physically discrete units suited as unitary dosages for the subject to be treated, each unit containing a predetermined quantity of active agent(s) calculated to produce the desired therapeutic effect in association with the required pharmaceutical carrier. The preparation can, for example, be enclosed in ampoules, disposable syringes or multiple dose vials made of glass or plastic.

Sterile injectable or infusible solutions can be prepared by incorporating the active compound in the required amount in an appropriate solvent, optionally with one or a combination of ingredients enumerated above, followed by filtered sterilization. Typically, solutions are free of endotoxin. Generally, dispersions are prepared by incorporating the active compound into a sterile vehicle, which contains a basic dispersion medium and optionally other ingredients. In the case of sterile powders for the preparation of sterile solutions, the usual methods of preparation are vacuum drying and freeze-drying (e.g., lyophilization) which yields a powder of the active ingredient plus any additional desired ingredient from a previously sterile-filtered solution thereof.

The foregoing recitation of materials to be used in compositions containing compounds of Formula (1) is intended to be exemplary and not limiting, it being understood that a variety of equivalent materials could also be used if desired.

Dosage

The effective oral dosage of the compounds of Formula (1), IGF-1, and HGH employed for the inhibiting aging of the inner ear, e.g. reversing of hearing loss, may vary depending on the particular compound employed and the severity of the condition being treated. However, in general, satisfactory results are obtained when the compounds of Formula (1), IGF-1, and HGH are each administered to humans at varying frequencies in a dosage of from about 0.1 to 2 mcg per kilogram (kg) of body weight, preferably given in divided doses one to six times a day, or in sustained release form. When the dosage of each of the compounds of Formula (1), IGF-1, and HGH is less than about 0.05 mcg/kg of body weight, the effect on preventing cell damage or apoptosis (i.e., inhibiting aging) is only marginal. When the daily dosage of each of the compounds of Formula (1), IGF-1, and HGH is at about 5 mcg/kg or greater the provision of such compounds becomes uneconomical. Further, such higher dosages are not required and may have an undesirable reverse effect, actually speeding up the aging process since the excess may upset the delicate balance of cochlear cell metastasis.

Dosage forms suitable for internal use comprise the active compound of Formula (1) and HGH in either acid or salt form or mixtures thereof in intimate admixture with a solid or liquid which are pharmaceutically acceptable carriers or diluents. The preferred pharmaceutical compositions from the standpoint of preparation and ease of administration are solid compositions, hard-filled capsules or tablets containing from about 20 to 100 mcg of active ingredient in acid or salt form. Other preferred and effective pharmaceutical compositions use a 3-day cyclic topical application of a liquid or gel containing from about 0.12 mcg IGF-1 and about 0.03 mcg HGH in a transdermal ear-spray using carbomer as carrier on a cotton swab or transdermal patch. These ear remedies slowly time-release IGF-1 and HGH into the cochlea, thus allowing for improved word recognition (see FIG. 3).

Methods and Results

Figure 6:
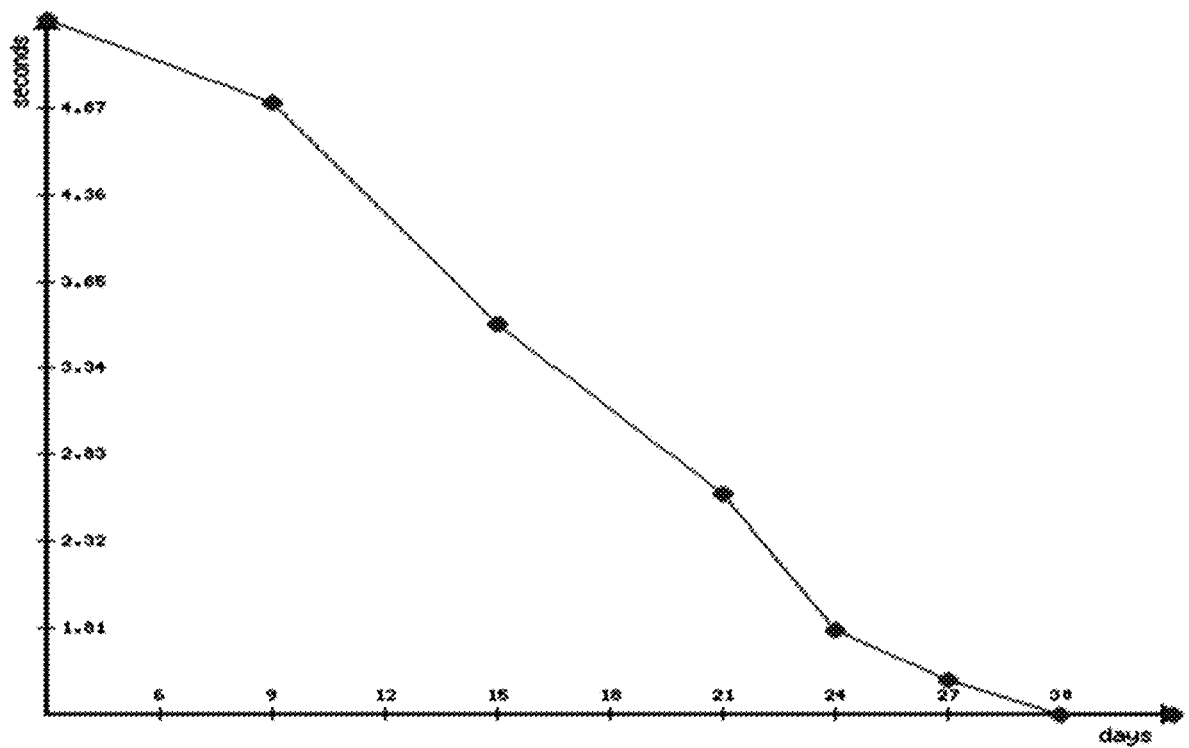
FIG. 6 is a graph illustrating improvement in neck skin plasticity in a single subject after injected with IGF-1 during a 30-day trial.

In accordance with the present invention, and referring to FIG. 6, experiments were conducted and showed improvement in neck skin plasticity in a single volunteer when the neck was injected with IGF-1 during a 30-day trial. Dorsal root neurons send pain signals to the brain via the spinal cord. IGF-1 mediates knockdown of its receptors IGF-1R, thus blocking myofascial pain in muscle tissue and improving skin plasticity. Neck trigger points were injected with a 31-gauge syringe at a 45-degree angle with 0.5 mcg IGF-1. Neck and back pain subsided within 10 minutes, and the nerve block lasted for approximately 6 hours (see also FIG. 3 indicating a 6-hour lag time before benefits are fully realized). Daily injections progressively increased skin plasticity during a 30-day trial. IGF-1 blocks pain transmission. Subsequently, IGF-1 is naturally absorbed in the body to promote ubiquitous healing and growth of other damaged tissues. IGF-1 does not cause a metabolic burden in the liver as in the case of opiates, lidocaine, and many steroids often used for pain management. IGF-1 trigger point injections are not addicting as in the case of many existing treatment alternatives (i.e. opiates). This is because IGF-1 lacks adverse side effects as often observed in other methods of pain management (e.g., lidocaine and other steroids). These positive effects are unique and non-obvious to practitioners of pain management.

A study was carried out with six presbycusic patients. After treatment with IGF-1 and growth hormone in a suitable topical carrier (see Examples 3 and 4 below), word recognition improved by a mean of 38.85 percent the following morning after a single dose using an ear canal topical application the previous evening (see FIGS. 3 and 4). These patients were treated with a maintenance dose as found in example 10. No side effects were observed except elevated tinnitus.

Figure 3:
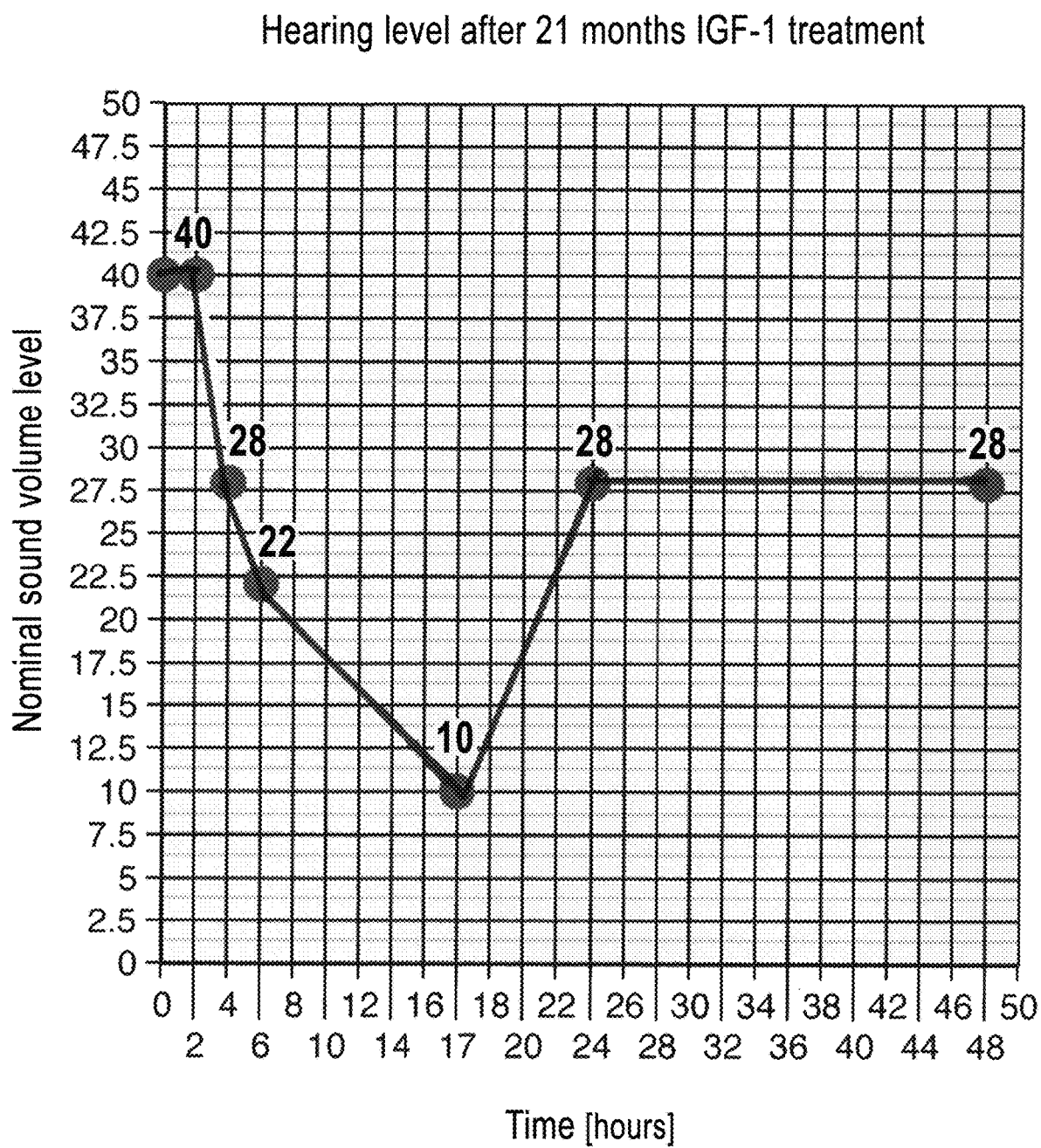
FIG. 3 is a graph showing dramatic hearing improvement six hours after Formula (1) topical treatment in the ear canals.

For patients with word recognition difficulties, application of IGF-1 and HGH in a transdermal ear-spray using carbomer on a cotton swab was found to be particularly effective. These ear remedies slowly time-release IGF-1 and HGH into the cochlea, thus allowing for improved word recognition (see FIG. 3). FIG. 3 is a graph showing dramatic hearing improvement six hours after Formula (1) topical treatment in the ear canals. As depicted in the graph of FIG. 3, maximum hearing was achieved after 17 hours, and subsequently, hearing returned to a somewhat elevated and steady-state level after 24 hours. Doses of 50 mcg, 75 mcg, 100 mcg and 200 mcg were administered to 6 human volunteers. Patients were tested with lists of 50 monosyllable words. After IGF-1 and HGH ear-spray application, comprehension was found to improve from below average to near average. Hearing improvements were found after approximately 6 hours, and maximum hearing is achieved after approximately 17 hours, thus demonstrating the biological action of IGF-1 and HGH and their receptor sites in this context (see FIG. 6).

Figure 5A:
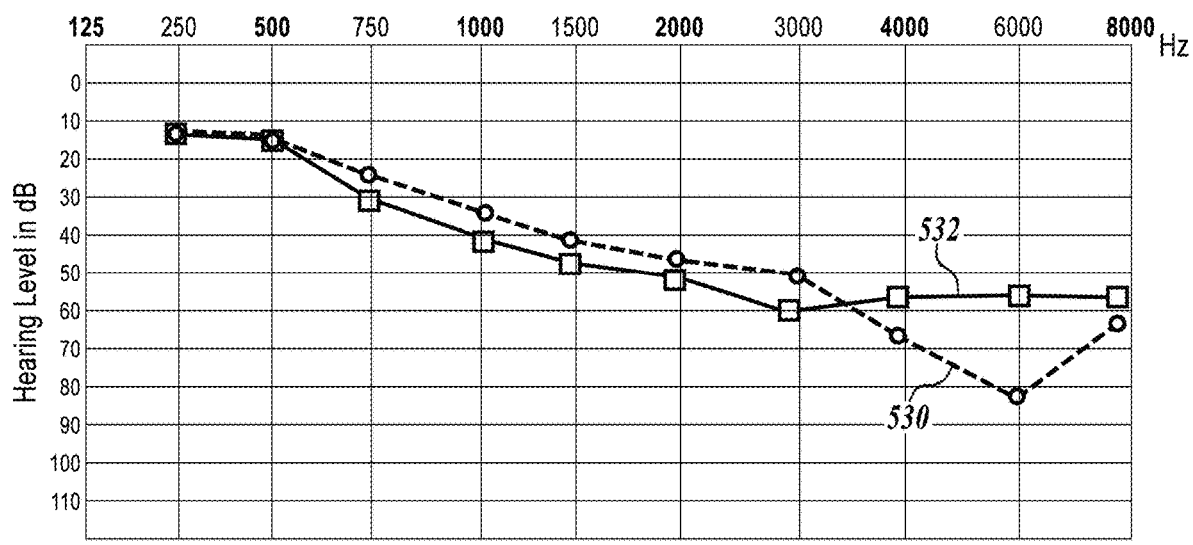
FIG. 5a illustrates two audiograms from the right ear.

FIG. 5A depicts two audiograms of the right ear. Data plot 530 (dashed lines with circles) depicts right ear hearing acuity levels on Jan. 15, 2016. Data plot 532 (solid line with squares) depicts the hearing acuity levels 4 months later on May 15, 2016. Hearing levels improved by as much as 40 dB at 6,000 Hz after 5 months treatment with IGF-1 and human growth hormone at a 5:2 ratio by weight.

Figure 5B:
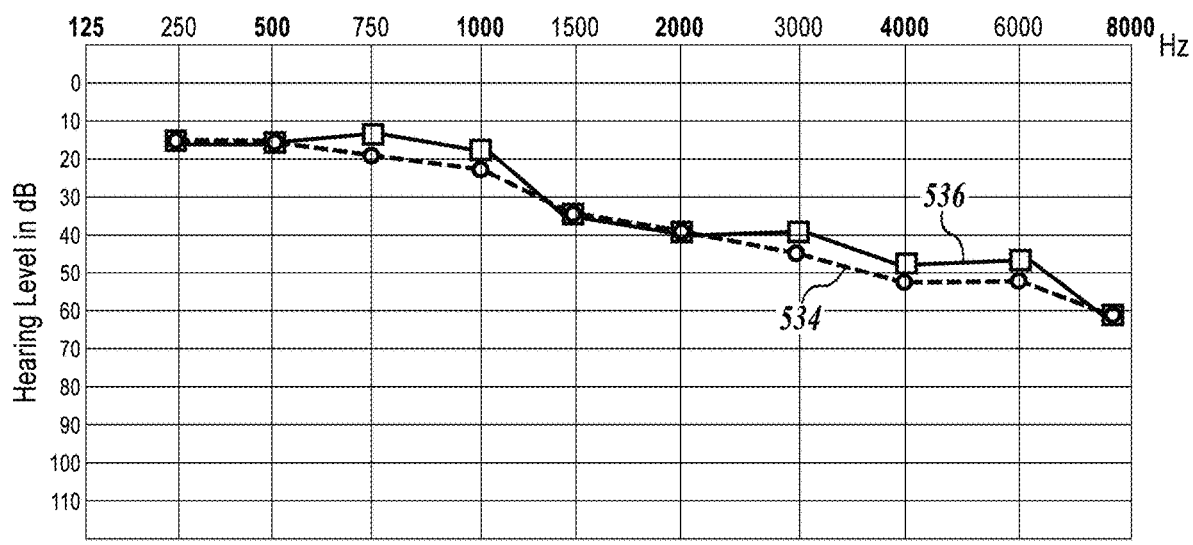
FIG. 5b illustrates two audiograms from the left ear.

FIG. 5B depicts two audiograms of the left ear resulting from the same methods and compositions used in FIG. 5A. Data plot 534 (dashed lines with circles) depicts hearing acuity levels on Jan. 15, 2016. Data plot 536 (solid line with squares) depicts the hearing acuity levels 4 months later on May 15, 2016. Hearing levels in the left ear improved significantly but not to the extent that the right ear hearing levels were improved. Although not reflected in FIGS. 5A and 5B, word recognition also improved significantly by approximately 34 percent. Near-normal hearing levels were achieved when this mixture was applied to the ear canals every third day rather than every day. Topical application at a frequency of every third day was found to be the optimal maintenance dose. Practitioners of the art do not know this method of improving word recognition. Optimal maintenance dose is defined as improved hearing volume up to 40 dB. Topical application at a frequency of every day (24 hours) only allowed improved hearing volume up to 22 dB as in the case when dosing with dexamethasone.

In the single-dose experiment, patients treated in the evening in accordance with the present invention awoke the following morning with some elevated noise from tinnitus and excellent hearing levels. Patients found that, in the morning, television or radio volume control needed to be turned down from a nominal 36 level to a 16±3 level. This is an indication that the bedtime topical application has worked to revive dying or poorly functioning hair cells by improving both hearing volume and word recognition, making hearing aids temporarily unnecessary. This dramatic morning increase is also accompanied with improvements in word recognition. In the morning following treatment, it was found that 6 patients dosed only one time recognized a mean of 48 out of 50 monosyllable words, and this result compares favorably with the previous evening when only a mean of 34-38 out of 50 monosyllable words (range 31-39 with a p value=1.0) were recognized.

Example 1

Tablets suitable for oral administration in accordance with practice of this invention may be prepared by conventional pharmacological techniques and may contain the following ingredients. While Insulin-like Growth Factor One (IGF-1) and HGH are disclosed in the Examples as the active ingredient, any compounds or mixture of compounds defined by the Formula (1) and HGH could be used. Such tablets are useful in the retardation of biological aging and hearing of mammals (i.e. improvement of hearing parameters).

| Ingredients | Weight |
| --- | --- |
| Insulin-like growth factor one (IGF-1) | 20 mcg |
| Human growth hormone (HGH) | 8 mcg |
| Sorbitol | 208 mg |
| Magnesium Stearate | 2 mg |

Example 2

Dry filled capsules suitable for oral administration in accordance with practice of this invention, which may contain the following ingredients, are prepared in a conventional manner.

| Ingredients | Weight |
| --- | --- |
| Insulin-like growth factor one (IGF-1) | 10 mcg |
| Human growth hormone (HGH) | 4 mcg |
| Inert solid diluent (lactose, sorbitol, starch, kaolin) | 170 mcg |

The Inert solid diluent acts to insure good mechanical flow in filling capsules. Examples of formulations for topical application provided in accordance with practice of this invention containing IGF-1 and HGH as the active ingredients are shown in Examples 3 and 4 below.

Example 3

| Ingredients | Composition % W/W |
| --- | --- |
| Insulin-like growth factor one (IGF-1) | 0.5 |
| Human growth hormone (HGH) | 0.2 |
| Purified water | 88.0 |
| Octyl Palmitate | 1.0 |
| Carbomer 933 | 1.0 |
| Lecithin | 1.0 |
| hydrogel | 1.0 |
| Glyceryl Sterate | 0.5 |
| Peg-100 Sterate | 0.5 |
| Ceteareth-20 | 0.5 |
| reticulan | 0.5 |
| Myristyl myristate | 0.5 |
| Mucopolyscaccharides | 0.5 |
| dihydroxy-3,20-dioxopregn-4-en-18-al | 0.5 |
| Jojoba oil | 0.5 |
| Collagen | 0.5 |
| Amino Acids | 0.5 |
| Paba | 0.5 |
| Vitamin A | 0.5 |
| Vitamin E | 0.5 |
| Allantoin | 0.5 |
| Imidazolidinyl urea | 0.5 |
| Vitamin B-5 | 0.5 |
| Methyl-propylparaben | 0.2 |
| Tea | 0.1 |
| Vitamin D | 0.1 |
| Natural fragrance | 0.1 |

Example 4

| Ingredients | Composition % W/W |
| --- | --- |
| Insulin-like growth factor one (IGF-1) | 2.0 |
| Human growth hormone (HGH) | 0.5 |
| Carbomer 933 | 1.0 |
| Crodacol CS-50 | 0.5 |
| Super Sterol Ester | 0.5 |
| Crodamol PMP | 1.0 |
| Polawax | 1.5 |
| Crosilk liquid | 5.0 |

The ingredients above are commercially available from sources such as Croda, Inc. (New York, N.Y.), SWS Silicones Corporation (Adrian, Mich.) and Sutton Laboratories, Inc. (Chatham, N.J.). Preferred compositions for topical administration contain from about 0.1% to about 20% by weight of the active ingredient of Formula (1), IGF-1 and HGH in either acid or salt form. Since the compounds of Formula (1) are active by themselves in retarding aging, i.e., in inhibiting damage to cells, they are contemplated as the only "active ingredient" in the compositions provided in accordance with practice of principles of this invention. It is preferred that the compositions comprise from about 0.1% to about 2% by weight of the active ingredient of Formula (1), IGF-1, and HGH. If the composition contains less than about 0.1% it will be only marginally effective and at greater than about 20% the economics would not be as favorable as desired and such high concentrations could possibly produce detrimental side effects. However, compositions for topical application where the active ingredient is in concentrations of from 0.001% to 90% by weight are contemplated.

The compositions described above when administered orally or topically, inhibit oxidation of imide bonds between collagen or elastin fibers to amide bonds. This is shown in FIG. 1 where a pair of collagen fibers (or a pair of elastin fibers) 110 are shown schematically placed adjacent to each other. The fibers owe their elasticity to reversible bonds that bind them together chemically. The two active sites that provide the bonds are the —CHO and —NH$_2$ moieties. Via a dehydration reaction 112 (or hydration reaction in reverse), the fibers form an imide compound 114 and are bonded together by the reversible imide bond 116. This reversible reaction of imide bonding is caused by the uptake and giving off of water (H2O), i.e. hydration and dehydration, respectively. Because the imide bonds open and close continuously, the collagen (or elastin) fibers glide freely past one another. This biochemical effect provides elasticity to the skin and arteries.

Figure 2:
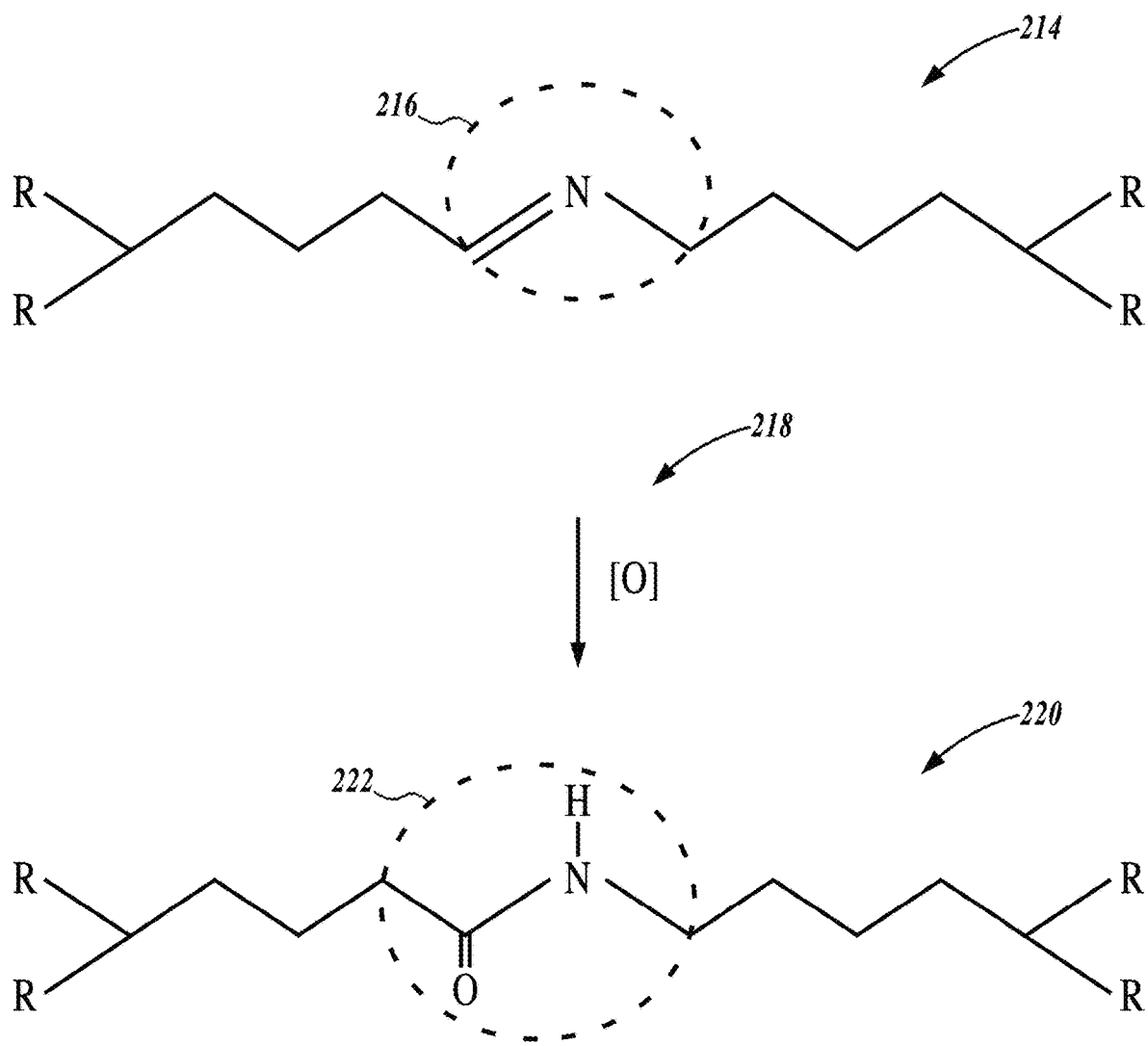
FIG. 2 is a schematic representation of two collagen fibers (R) or two elastin fibers (R) joined together by an amide bond which is further oxidized to a permanent amide bond.

FIG. 2 shows the imide compound 214 of FIG. 1 that includes the imide bond 216 and its conversion to an amide compound 220 via an oxidation reaction. As a result of oxidation reaction 218, the imide bond 216 is converted to an amide bond 222. Humans stop growing and maturing after 20-30 years. During aging, the cochlea, skin and arteries of man and other mammals become increasingly inelastic. This inelasticity is largely the result of the oxidation of the imide bond to the amide bond. The amide bond 222 is permanent and results in an undesirably, permanent rigid linking between collagen and elastin fibers especially in the human cochlea. The structures of FIGS. 1 and 2 correspond to Examples 4 (above) and 5 (below).

Example 5

As previously indicated, the compounds of Formula (1), IGF-1, and HGH are useful because they possess pharmacological activity in mammals including humans. In one aspect of practice of techniques of this invention, the compounds of Formula (1), IGF-1, and HGH are useful in retarding the aging phenomena of skin wrinkling. In this example, twenty-four (24) Uppsala mice were topically treated with a lotion as described in Example 4 (provided by Anticimax of Sodertalje, Sweden) containing 0.01 mg IGF-1 and 0.004 mg HGH from the twelfth to thirty-sixth month of their lifespan. Six (6) control mice topically treated with the same lotion without these active ingredients as the aforementioned 24 mice.

The Formula (1), IGF-1, and HGH treated mice were visually more youthful and healthy at 26 months of age than control mice. The last remaining control mouse showed significant hearing loss, hair loss, pigmentation loss, poor eyesight and difficulty in movement as compared with the four Formula (1) treated mice that were also still living at this stage of the experiment. Especially apparent was the greater skin wrinkling in control mice versus Formula (1), IGF-1, HGH treated mice. Control mice did not react as readily to a bell announcing feeding time, as did the Formula (1), IGF-1, and HGH treated mice. The increased wrinkling and hearing loss are indicative of collagen and elastin hardening and cross-linking via the conversion of imide to amide bonds as discussed above.

Example 6

Figure 4:
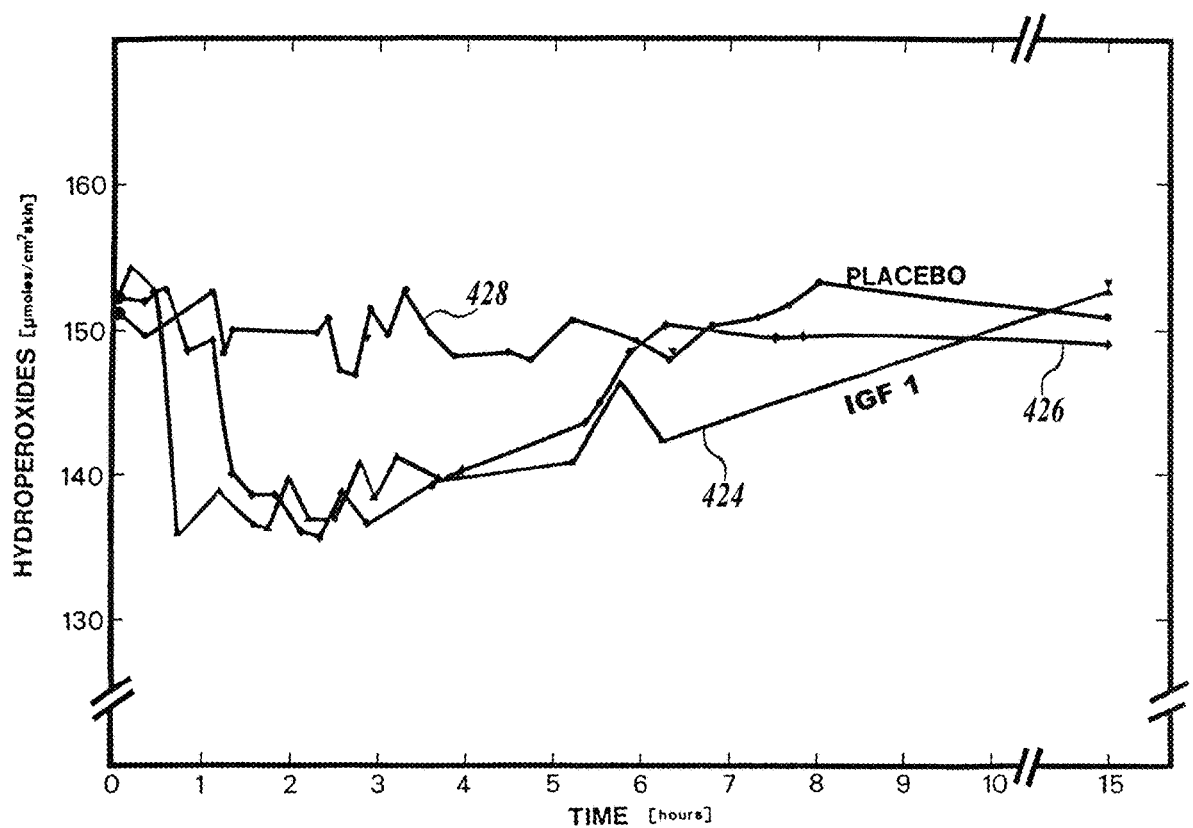
FIG. 4 illustrates the pharmacokinetics of topical IGF-1 application showing a gradual return to a normal level of 150 μmol/cm after approximately 6 hours.

Turning to FIG. 4, the results of a double-blind time study using a composition containing 0.02% by weight Formula (1) can be seen. This composition was the same as the composition set forth in Example 3 with the exception that the percentage of water was reduced to 86%. Starting at time zero, 10 milliliters of this cream was vigorously applied topically onto the skin of the forehead of a volunteer. Measurements were taken at different intervals using non-invasive, reflective, near-infrared spectroscopy. The methods of non-invasive, reflective, near infrared spectroscopy used in this example are set forth in detail in R. Lippman, "Rapid in vivo Quantification and Comparison of Hydroperoxides and Oxidized Collagen in Aging Mice, Rabbits and Man", Experimental Gerontology, Vol. 20, pp. 1-5, 1985, which is incorporated herein by this reference. Results showed that lipid hydroperoxides in the other skin layers and microvascularization decreased from about 190 to 148 µmol/cm2 skin after about one hour. The pharmacokinetics of topical IGF-1 application showed a gradual return to a normal level of 170 µmol/cm2 level after approximately 6 hours. This experiment showed that facial skin and skin unsaturated lipids are preserved, and damage is prevented by topically applying Formula (1), IGF-1, and HGH cream as set forth in Example 3.

Example 7

Glial cells from a human brain were cultivated by monolayering on Petri dishes. Cellular ATP production was measured using bioluminescent methods (luciferin, luciferase and photomultiplier detection). Formula (1), IGF-1, and HGH (5:2 ratio) was added to various cultures to a level of 0.2% w/v and an increase in steady state ATP production was observed.

Example 8

A single patient with diagnosed severe deafness improved his hearing by 30 dB at 3,000 Hz when 25 mcg of Formula (1) and 5 mcg of HGH were consumed orally twice daily for seven months. No improvements in word recognition were observed. Hearing volume in the right ear improved from 26 to 78% and in the left ear from 7 to 54%. The corresponding results of this example are shown in FIGS. 3 and 5.

Example 9

Turning to FIG. 4, which is a graph of results of a pharmacokinetic time-course (double-blind) study of single doses of Formula (1) and HGH applied topically as in Example 4 to the ear canals of human volunteers at time zero. Single doses of IGF-1 of 1 mcg, 2 mcg, 3 mcg and 4 mcg combined with HGH of 0.4 mcg, 0.8 mcg, 1.2 mcg, and 1.6 mcg were given to 6 volunteers who had fasted at least 12 hours (overnight). The result is plotted as line 424.

Placebos were given to two (2) other volunteers as shown in plots 426 and 428. Using the above referenced non-invasive technique called reflective, near-infrared spectroscopy, changes in the microvascular concentrations of lipid hydroperoxides were monitored during 8-hour test periods. The graph of FIG. 4 plots the concentration of hydroperoxides in the skin in μmole/cm2 on the vertical axis (as measured by the near-infrared spectroscopy technique) versus time in hours on the horizontal axis. Subjects received single doses of IGF-1 and HGH and placebos topically, respectively.

The results, as can be seen in FIG. 4, show that IGF-1, Formula (1) and HGH were absorbed into the blood stream after about 1 to 2 hours upon topical administration into ear canals. IGF-1 and HGH reduced levels of microvascular lipid hydroperoxides at least 17% during the 4 to 8-hour study periods. A nearly flat line at approximately 150 μmol/cm (not shown on the graph) was recorded for the two volunteers who received placebos. It is concluded that IGF-1 Formula (1) and HGH is an effective neutralizer of toxic byproducts of oxygen metabolism, i.e. lipid hydroperoxides, when taken at regular intervals of at least 6 hours, 3 times daily. This embodiment of this invention was also effective in improving word recognition. Using lists of 50 monosyllabic words, 6 patients recognized 48 words the morning after treatment. This result compares favorably with the previous evening before treatment when only mean of 34.57 monosyllabic words were recognized.

Example 10

FIGS. 5A and 5B depict two audiograms of results of a pharmacokinetic time-course (double-blind) study of single doses of Formula (1) IGF-1 0.10 mcg, and human growth hormone 0.04 mcg were applied topically using a topical lotion in the ear canals to human volunteers at time zero. The lotion composition was as set forth in Example 3 with the exception that the percentage of water was reduced from 88% to 86%. Starting at time zero, 0.3 milliliters of this topical lotion was vigorously applied topically onto the skin of two ear canals of a volunteer. Measurements were taken at different decibel intervals recorded on the audiograms for a period of five months. As shown, hearing volume increased by as much as 40 decibels (dB) at 6,000 Hz after 5-month treatment with IGF-1 and human growth hormone (4:1 ratio by weight). Tinnitus was the observed side effect in these studies. The composition used in accordance with this embodiment can include metabolites of IGF-1 and human growth hormone, including but not limited to, the hormone aldosterone.

With respect to the present invention, a five-month study of 6 volunteers was conducted and demonstrated that word recognition improved significantly by 38.85 percent. Nakagawa et al. did not observe this unique and non-obvious result of significant augmentation in word recognition. Near normal hearing in severely deficient patients was observed especially when this dose was applied every three days instead of everyday. As in the case of some hormones, IGF-1 must be allowed to cycle intratympanically between high and low concentrations in order to achieve a preferred clinical effect. The IGF-1 was combined with human growth hormone in a 5 to 2 ratio. A third benefit was a general improvement in hearing range at the middle frequency levels of 6,000 Hz and higher, a level where many older human volunteers are completely deaf.

While there have been described herein what are considered to be preferred and exemplary embodiments of the present invention, i.e. methods and compositions for inhibiting or reversing hearing loss (and damage to cochlea cells) in mammals caused by hormone deficiencies or toxic byproducts of oxygen metabolism, other modifications of the invention shall be apparent to those skilled in the art from the teachings herein. It is noted that the embodiments disclosed are illustrative rather than limiting in nature and that a wide range of variations, modifications, changes, substitutions are contemplated in the foregoing disclosure and, in some instances, some features of the present invention may be employed without a corresponding use of other features. Many such variations and modifications may be considered desirable by those skilled in the art based upon a review of the foregoing description of preferred embodiments. Accordingly, it is appropriate that the appended claims be construed broadly and in a manner consistent with the scope of the invention.

What is claimed is:

1. A method for improving hearing parameters in a human by intratympanically administering a dosage, within the range of 0.1 mcg per kilogram of body weight to 2 mcg per kilogram of body weight, of a pharmaceutically acceptable composition comprising a compound or mixture of compounds containing insulin-like growth factor 1 (IGF-1) and human growth hormone, wherein the hearing parameters include hearing volume, hearing range and word recognition.

2. The method according to claim 1 wherein the composition is administered in at a frequency that allows the IGF-1 to cycle intratympanically between high and low concentrations.

3. The method according to claim 1 wherein the dosage is administered at a frequency of every three days to allow the IGF-1 to cycle intratympanically between high and low concentrations.

4. The method of claim 1 wherein the composition is administered topically in the form of a cream, lotion, or serum.

5. The method of claim 1 wherein the human's hearing volume is improved by up to 40 decibels.

6. The method of claim 1 wherein the human's hearing range is improved above 6,000 Hz.

7. The method of claim 1 wherein the human's word recognition is improved by at least 30 percent.

8. The method of claim 1 wherein the composition contains relative amounts of IGF-1 and human growth hormone in a ratio of 5:2 by weight.

9. The method of claim 1 wherein the composition contains from 0.1% to 20% by weight of IGF-1 and HGH.

* * * * *